United States Patent [19]
Wilson, Jr. et al.

[11] Patent Number: 6,048,992
[45] Date of Patent: Apr. 11, 2000

[54] METALLOCENE COMPOUNDS FROM AMINO ALCOHOL-DERIVED LIGANDS

[75] Inventors: Robert B. Wilson, Jr., Palo Alto; Gary A. Koolpe, San Jose, both of Calif.

[73] Assignee: SRI International, Menlo Park, Calif.

[21] Appl. No.: 09/276,398

[22] Filed: Mar. 25, 1999

[51] Int. Cl.[7] .............................. C07F 17/00; C07F 7/00; C08F 4/64

[52] U.S. Cl. .............................. 556/10; 556/11; 556/43; 556/52; 556/58; 556/408; 526/126; 526/170; 526/348; 526/351; 526/352; 526/943; 502/120; 502/158

[58] Field of Search .............................. 556/408, 10, 11, 556/43, 52, 58; 502/120, 158; 526/126, 170, 348, 351, 352, 943

[56] References Cited

U.S. PATENT DOCUMENTS

| | | | |
|---|---|---|---|
| 4,471,132 | 9/1984 | Hallgren | 556/410 |
| 4,491,669 | 1/1985 | Arkles et al. | 556/410 |
| 5,439,994 | 8/1995 | Inoue et al. | 526/114 |
| 5,585,508 | 12/1996 | Kuber et al. | 556/11 |
| 5,631,202 | 5/1997 | Ewen | 502/117 |

OTHER PUBLICATIONS

Amor et al. (1997), "Remarkably Robust Group 4 Metal Half–Sandwich Complexes Containing Two Higher Alkyl Ligands: X–Ray Structure and Reactivity of the Di–η–Butyl Complex [Hf($\eta^5$:$f^1$:$\eta^1$–$C_5Me_4SiMe_2NCH_2CH_2OMe$)"$Bu_2$]," *Organometallics* 16:4765–7467.

Broene et al. (1995), "Zirconocene Complexes of Unsaturated Organic Molecules: New Vehicles for Organic Synthesis" *Science* 261:1696–1701.

du Plooy et al. (1995), "Coordination Properties of Novel Tridentate Cyclopentadienyl Ligands in Titanium and Zirconium Complexes," *Organometallics* 14:3129–3131.

Duthaler et al. (1992), "Chiral Titanium Complexes for Enantioselective Addition of Nucleophiles to Carbonyl Groups," *Chem. Rev.* 92:807–832.

Halterman (1992) "Synthesis and Applications of Chiral Cyclopentadienltmetal Complexes," *Chem. Rev.* 92:965–994.

Hoyveda et al. (1996), "Enantioselective C–C and C–H Bond Formation Mediated or Catalyzed by Chiral ebthi Complexes of Titanium and Zirconium," *Angew. Chem. Int. Ed. Engl.* 35:1262–1284.

Hultzsch et al. (1997), "Polymerization of ε–Caprolactone Using Heterobimetallic Lanthanocene Complexes," *Macromal Rapid Commun.* 18:809–815.

(List continued on next page.)

*Primary Examiner*—Porfirio Nazario-Gonzalez
*Attorney, Agent, or Firm*—Dianne E. Reed; Reed & Associates

[57] ABSTRACT

A method is provided for synthesizing metallocene compounds useful as polymerization catalysts and the like. The method involves (a) preparation of an amino alcohol-derived ligand by reacting a silane reactant with an amino alcohol in the presence of base, followed by (b) metallation of the ligand so provided. The metallocenes may be provided in chiral form when the amino alcohol contains an asymmetric center, and are thus useful in catalyzing stereospecific polymerization and other stereospecific bond formation reactions.

48 Claims, 2 Drawing Sheets

LIGAND SYNTHESIS:

METALLATION:

OTHER PUBLICATIONS

Hultzsch et al. (1998), "Synthesis and Characterization of Yttrium Complexes Containing a Tridentale Linked Amido–Cyclopentadienyl Ligand," *Organometallics* 17:485–488.

Narula et al. (1984), "Coordination Compounds of Organometallic Bases of Group IV Elements: PArt V—Reactions of Benzylamino/anilino–tris(2–chloroethoxy)/bis(2–choroethoxy)alkoxy/bis(2–chloroethoxy)methyl/(2–chlorethoxy)dialkoxy–silanes with Titanium (IV) & Tin (IV) Chlorides," *Indian Journal of Chemistry* 23A:661–663.

Pikies et al. (1983), "Darstellung und spektroskopische Eigenschaften von Alkoxyaminosilanen $(RO)_1Me_{3-n}SiNHC_6H_4X$," *Z. Anorg. allg. Chem.* 503:224–230 (English language abstract included).

Viso et al. (1994), "Kinetic Resolution of Racemic Disubstituted 1–Pyrroluhes via Asymmetric Reduction with a Chiral Titanocene Catalyst," *J. Am. Chem. Soc.* 116:9373–9374.

Waymouth et al. (1990), "Enantioselective Hydrogenation of Olefins with Homogeneous Ziegler–Natta Catalysts," *J. Am. Chem. Soc.* 112:4911–4914.

LIGAND SYNTHESIS:

METALLATION:

6,048,992

METALLOCENE COMPOUNDS FROM AMINO ALCOHOL-DERIVED LIGANDS

TECHNICAL FIELD

This invention relates generally to metallocenes, and more particularly relates to novel metallocene compounds, preferably chiral metallocenes, that are useful as catalysts, and to methods for synthesizing the novel metallocenes. The invention additionally relates to amino alcohol-derived ligands useful for preparing the novel metallocenes via metallation, and to methods of using the metallocene compounds, e.g., in catalysis.

BACKGROUND

Many processes and catalysts are known for the preparation of homopolymeric or copolymeric olefins and other polymers. Ziegler-Natta catalyst compositions, developed in the 1950s, were found to be particularly useful in the preparation of polyolefins. These catalyst compositions comprise transition metal compounds such as titanium tetrachloride and an alkylaluminum (e.g., triethylaluminum) cocatalyst. The systems were found to be advantageous because of their high activity, and were largely consumed during polymerization.

More recent catalyst systems for use in preparing polyolefins and other polymers are "metallocenes." The term "metallocene" was initially coined in the early 1950s to refer to dicyclopentadienyliron, or "ferrocene," a structure in which an iron atom is contained between and associated with two parallel cyclopentadienyl groups. In general, the term is now used to refer to organometallic complexes in which a metal atom (not necessarily iron) is coordinated to at least one cyclopentadienyl ring ligand.

In contrast to the traditional Ziegler-Natta catalysts, metallocenes can provide a polymer composition containing a plurality of polymer molecules of substantially the same molecular structure. That is, if one high purity metallocene catalyst is used, the variance in the composition or molecular weight of the individual polymer molecules produced is minimal. With metallocenes, then, it is possible to control compositional distribution and other aspects of polymer molecular structure with unprecedented precision. Metallocene catalysts have other advantages as well. For example, metallocenes: (a) can polymerize almost any vinyl monomer irrespective of molecular weight or steric considerations; (b) provide the ability to control vinyl unsaturation in the polymers produced; (c) enable polymerization of α-olefins with very high stereoregularity to give isotactic or syndiotactic polymers; and (d) can function as hydrogenation catalysts for polymers as well as monomers. A. D. Horton, "Metallocene Catalysis: Polymers by Design," *Trends Polym. Sci.* 2(5):158–166 (1994), provides an overview of metallocene catalysts and their advantages, and focuses on now-conventional complexes of Group IV transition metal complexes and cyclopentadienyl ligands (Cp$_2$MX$_2$, wherein Cp represents a cyclopentadienyl ligand, M is Zr, Hf or Ti, and X is Cl or CH$_3$).

Metallocenes have also been found to be useful in catalyzing other types of reactions, i.e., reactions other than polymerization reactions. For example, metallocenes have been used as hydrogenation catalysts, dehydrocoupling catalysts, cyclization catalysts, substitution reaction catalysts, hydroformylation catalysts, carbomagnesation catalysts and hydrosilylation catalysts. See, e.g., Lu et al. (1997), *Lanzhou Inst. Chem. Phys.* 11(6):476–483; Halterman (1992), "Synthesis and Applications of Chiral Cyclopentadienyl Complexes," *Chem. Rev.* 92:965–994; and Hoveyda et al. (1996), "Enantioselective C—C and C—H Bond Formation Mediated or Catalyzed by Chiral ebthi Complexes of Titanium and Zirconium," *Angew. Chem.* 35:1262–1284. Thus, metallocenes are extremely versatile and valuable catalysts. However, prior metallocene catalysts have proved to be relatively difficult and time-consuming to synthesize, requiring expensive equipment, extreme reaction conditions, and multi-step processes that ultimately result in a low yield of the desired product. Accordingly, there is a need in the art for new metallocene catalysts that can be synthesized without any of the aforementioned problems. That is, it would be desirable to have a simple, straightforward method for preparing chiral metallocenes that can be used in stereospecific catalysis, to be used in the stereospecific polymerization of olefins as well as in other stereospecific bond formation reactions. The present invention is addressed to the aforementioned needs in the art.

SUMMARY OF THE INVENTION

Accordingly, it is an object of the invention to provide a method for synthesizing metallocene compounds useful as catalysts, wherein the metallocenes can, if desired, be prepared as chiral compounds.

It is another object of the invention to provide such a method which involves preparing an amino alcohol-derived ligand from a silane reactant and an amino alcohol, and metallating the amino alcohol-derived ligand so prepared.

It is still another object of the invention to provide a method for synthesizing amino alcohol-derived ligands useful for providing metallocene compounds via a metallation reaction.

It is yet another object of the invention to provide novel metallocene compounds useful as catalysts.

It is an additional object of the invention to provide amino alcohol-derived ligands useful for preparing metallocene compounds via a metallation reaction.

It is a further object of the invention to provide a method for synthesizing polymers, particularly polyolefins, using the present metallocene compounds as polymerization catalysts.

Additional objects, advantages and novel features of the invention will be set forth in part in the description which follows, and in part will become apparent to those skilled in the art upon examination of the following, or may be learned by practice of the invention.

In one aspect of the invention, then, a method is provided for synthesizing a metallocene compound, the method comprising: (a) preparing an amino alcohol-derived ligand by reacting a silane reactant having two leaving groups with an amino alcohol, in the presence of base; and (b) metallating the amino alcohol-derived ligand so prepared. In a preferred embodiment, the amino alcohol is a chiral compound, so that the metallocene ultimately prepared therefrom contains at least one asymmetric center, enabling catalysis of stereospecific reactions.

While the novel metallocenes may be used to catalyze any reactions for which metallocene catalysts are generally known to be useful, the present metallocene compounds are particularly useful as polymerization catalysts. One important application use of the novel metallocenes is in catalyzing the polymerization of addition polymerizable monomers containing one or more degrees of unsaturation, to prepare polyolefins or other polymers. Another application of the present compounds is in catalyzing the polymerization of aromatic monomers such as styrene, indene, or the like.

With respect to the preparation of polyolefins, such polymers, as is known in the art, can be prepared having a variety of steric configurations deriving from the manner in which each monomer is added to the growing polymer chain. Four basic configurations are commonly recognized for polyolefins: atactic, in which monomer orientation is random; isotactic, in which each monomer is incorporated into the polymer in the same configuration; syndiotactic, in which the configuration of monomers alternates along a polymer chain; and hemi-isotactic, in which unique and regularly repeating stereochemistries are present within a single polymer chain. The present metallocenes are useful for preparing polymers of desired tacticity, insofar as the chiral catalysts can be used to catalyze stereospecific polymerization. Generally, metallocene catalysts having $C_2$ symmetry will give rise to isotactic polymers, while those catalysts having $C_s$ symmetry will give rise to syndiotactic polymers.

DETAILED DESCRIPTION OF THE INVENTION

Figure 1:
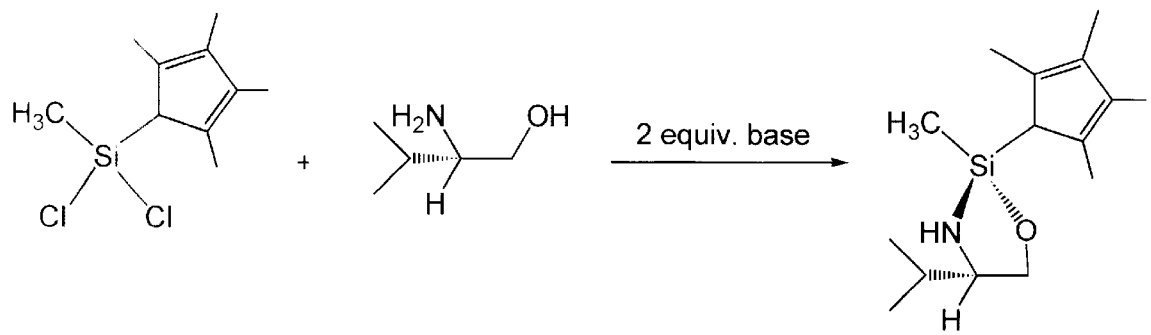
FIG. 1 schematically illustrates synthesis of a metallocene compound using the methodology of the invention.
Figure 1:
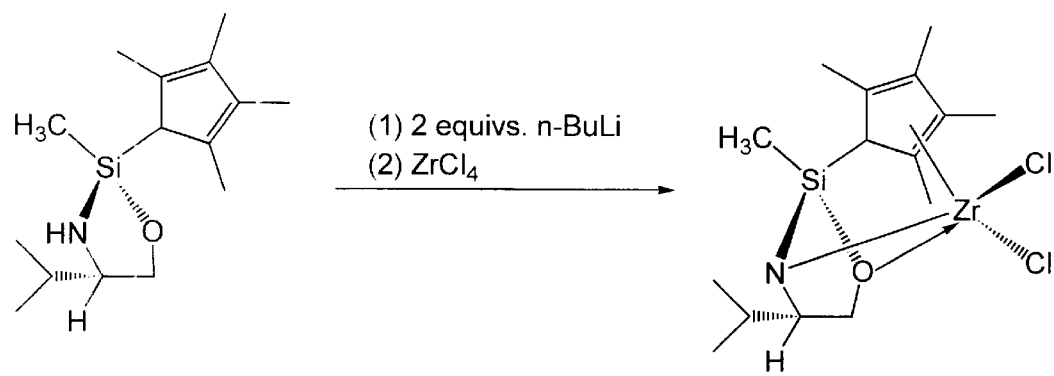
Figure 2:
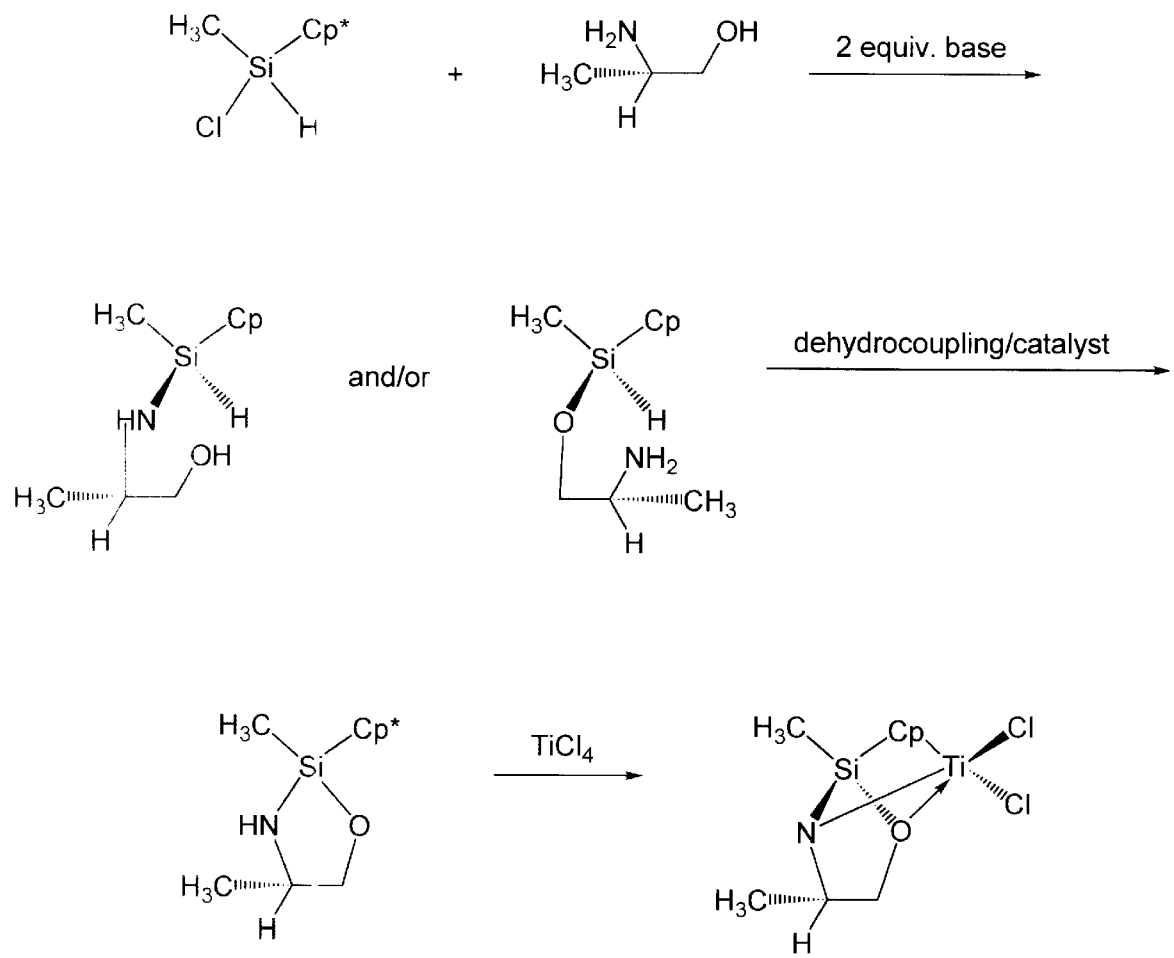
FIG. 2 schematically illustrates an alternative synthetic route to a metallocene compound, again using the methodology of the invention.

Before the present compounds, compositions and methods are disclosed and described, it is to be understood that unless otherwise indicated this invention is not limited to specific reactants, reaction conditions, ligands, metallocene structures, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a leaving group" as in a moiety "substituted with a leaving group" includes more than one leaving group, such that the moiety may be substituted with two or more such groups. Similarly, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene (—$CH_2$—$CH(CH_3)$—$CH_2$—), hexylene (—$(CH_2)_6$—), and the like. "Lower alkylene" refers to an alkylene group of 1 to 6, more preferably 1 to 4, carbon atoms.

The term "alkenyl" as used herein refers to a branched or unbranched hydrocarbon group of 2 to 24 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 2 to 12 carbon atoms and 2 to 3 carbon-carbon double bonds. The term "lower alkenyl" intends an alkenyl group of 2 to 6 carbon atoms, preferably 2 to 4 carbon atoms, containing one —C=C— bond. The term "cycloalkenyl" intends a cyclic alkenyl group of 3 to 8, preferably 5 or 6, carbon atoms.

The term "alkenylene" refers to a difunctional branched or unbranched hydrocarbon chain containing from 2 to 24 carbon atoms and at least one carbon-carbon double bond. "Lower alkenylene" refers to an alkenylene group of 2 to 6, more preferably 2 to 5, carbon atoms, containing one —C=C— bond.

The term "alkynyl" as used herein refers to a branched or unbranched hydrocarbon group of 2 to 24 carbon atoms containing at least one —C≡C— bond, such as ethynyl, n-propynyl, isopropynyl, n-butynyl, isobutynyl, t-butynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— bond.

The term "alkynylene" refers to a difunctional branched or unbranched hydrocarbon chain containing from 2 to 24 carbon atoms and at least one carbon-carbon triple bond. "Lower alkynylene" refers to an alkynylene group of 2 to 6, more preferably 2 to 5, carbon atoms, containing one —C≡C— bond.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "amino alcohol" as used herein refers to a chemical entity containing both an amino group —$NH_2$ and a hydroxyl moiety.

The term "aryl" as used herein refers to an aromatic species containing 1 to 5 aromatic rings, either fused or linked, and either unsubstituted or substituted with 1 or more substituents typically selected from the group consisting of —$(CH_2)_x$—$NH_2$, —$(CH_2)_x$—COOH, —$NO_2$, halogen and lower alkyl, where x is an integer in the range of 0 to 6 inclusive as outlined above. Preferred aryl substituents contain 1 to 3 fused aromatic rings, and particularly preferred aryl substituents contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —$(CH_2)_j$—Ar wherein j is an integer in the range of 1 to 24, more typically 1 to 6, and Ar is a monocyclic aryl moiety.

The term "arylene" refers to a difunctional aromatic moiety; "monocyclic arylene" refers to a cyclopentylene or phenylene group that may or may not be substituted. These groups may be substituted with up to four ring substituents as outlined above.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocycle consists of carbon atoms and from one to four heteroatoms selected from the group consisting of nitrogen, oxygen and sulfur. As used herein, the terms "nitrogen heteroatoms" and "sulfur heteroatoms" include any oxidized form of nitrogen and sulfur, and the quaternized form of any basic nitrogen. Examples of heterocyclic groups include piperidinyl, morpholinyl and pyrrolidinyl.

"Halo" or "halogen" refers to fluoro, chloro, bromo or iodo, and usually relates to halo substitution for a hydrogen atom in an organic compound. Of the halos, chloro and fluoro are generally preferred.

"Hydrocarbyl" refers to unsubstituted and substituted hydrocarbyl radicals containing 1 to about 20 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. "Hydrocarbylene" refers to unsubstituted and substituted hydrocarbylene moieties containing 1 to about 20 carbon atoms. The term "lower hydrocarbylene" intends a hydrocarbylene group of one to six carbon atoms, preferably one to four carbon atoms.

The term "leaving group" is used in its conventional sense to refer to a molecular moiety that may be displaced via a substitution reaction, typically via nucleophilic attack. In the present context, the "leaving groups" such as alkoxy or halide moieties are bound to a silicon atom, and are displaced by the amino and hydroxyl moieties of an amino alcohol.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

A "heterogeneous" catalyst as used herein refers to a catalyst which is supported on a carrier, typically although not necessarily a substrate comprised of an inorganic, solid, particulate porous material such as silicon and/or aluminum oxide.

A "homogeneous" catalyst as used herein refers to a catalyst which is not supported but is simply admixed with the initial monomeric components in a suitable solvent.

A "metallocene" refers to an organometallic complex in which a metal atom is coordinated to at least one cyclopentadienyl ring ligand.

As used herein all reference to the Periodic Table of the Elements and groups thereof is to the version of the table published by the Handbook of Chemistry and Physics, CRC Press, 1995, which uses the IUPAC system for naming groups.

In a first embodiment, then, a method is provided for synthesizing a metallocene compound, the method comprising the steps of: (a) reacting, in the presence of base, (i) a silane substituted with an aromatic moiety and two leaving groups with (ii) an amino alcohol, under conditions effective to promote coupling therebetween and provide a silicon-containing, nitrogen-containing ligand; and contacting the ligand so prepared with a metal compound under reaction conditions effective to bring about metallation. Preferably, the amino alcohol contains at least one asymmetric center, which is typically although not necessarily at a carbon atom.

The silane reactant will generally have the structural formula (I)

(I)

wherein the various substituents are defined as follows.

The L may be the same or different, and represent the leaving groups. Examples of suitable leaving groups include, but are not limited to, hydrido, alkoxy, amine, amide and halide, typically lower alkoxy, e.g., methoxy, ethoxy, propoxy, etc., dimethylamine, diethylamine, cyclohexylamine, morpholine, etc., and chloro.

R is substituted or unsubstituted hydrocarbyl. Preferred R groups are alkyl and alkenyl. In the latter case, the presence of an alkenyl substituent, which typically contains a double bond at a location within the molecule that ultimately allows for further modification of the metallocene. Most preferably, R is lower alkyl or lower alkenyl.

Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are preferably fused. Examples of suitable Ar groups include, but are not limited to, cyclopentadienyl, tetramethylcyclopentadienyl, methylcyclopentadienyl, methyl-t-butylcyclopentadienyl, t-butylcyclo-pentadienyl, isopropylcyclopentadienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-t-butylindenyl, 3-trimethylsilylindenyl, 2-methyl-4-phenylindenyl, 2-ethyl-4-phenylindenyl, 2-methyl-4-naphthylindenyl, 2-methyl4-isopropylindenyl, 4,5-benzoindenyl, 2-methyl4,5-benzoindenyl, 2-methyl-α-acenaphthylindenyl, 2-methyl4,6-diisopropylindenyl, fluorenyl, 4-methylfluorenyl and 2,7-di-t-butylfluorenyl. Preferred Ar groups thus include cyclopentadienyl, cyclopentadienyl substituted with one to four lower alkyl substituents, indenyl, fluorenyl and indolyl, with cyclopentadienyl, tetramethylcyclo-pentadienyl, indenyl and fluorenyl particularly preferred.

The amino alcohol has the structural formula (II)

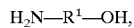

(II)

wherein $R^1$ is substituted or unsubstituted hydrocarbylene, preferably alkylene, and most preferably lower alkylene substituted with one through four lower alkyl, phenyl or benzyl groups.

Reaction of the silane (I) with amino alcohol (II) is conducted in the presence of base so as to facilitate coupling of the silane to both the amino substituent and the hydroxyl group. The coupling reaction gives rise to the ligand (III)

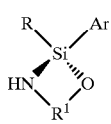
(III)

in which Ar, R and $R^1$ are as defined above.

This amino alcohol-derived ligand may then be metallated by contacting the ligand with a metal compound $MX_2Y_2$ wherein M is a Group IVA, Group VA or Group VIA metal, the X are independently selected from the group consisting of halide, lower alkoxy, lower alkyl and amido, and the Y are independently selected from the group consisting of halide and lower alkoxy. Preferably, prior to contacting the ligand with the metal compound, the ligand is treated with a dehydrogenation reagent, e.g., an organolithium compound, an organotin compound, or a Grignard reagent. Specific such compounds include without limitation methyllithium, n-butyllithium, tri (t-butyl) tin and methylmagnesium bromide. As will be appreciated by those skilled in the art, the metallation reaction in this case is what is commonly termed "transmetallation." The metallation reaction provides a metallocene having the formula (IV)

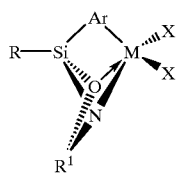
(IV)

Generally, although not necessarily, the amino alcohol (II) has the structural formula (IIa)

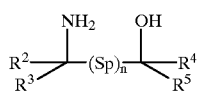
(IIa)

wherein $R^2$, $R^3$, $R^4$ and $R^5$ are independently selected from the group consisting of hydrogen, alkyl and aryl, and are preferably selected from the group consisting of hydrogen, lower alkyl, phenyl and benzyl, and Sp is an optional spacer moiety, i.e., n is 0 or 1. Generally Sp, if present, introduces only one or two atoms between the adjacent carbon atoms. Preferably, Sp is selected from the group consisting of —$CR^7_2$—, —$CR^7_2$—$CR^7_2$—, —O—, —S—, —$NR^7$—, —$BR^7$—, —C(O)— and combination thereof, wherein $R^7$ is hydrogen, lower alkyl or aryl, and n is 0 or 1. The asymmetric center, which as noted above is present in a preferred embodiment, is typically at the carbon atom that is directly bound to the primary amino moiety, or at the carbon atom that is directly bound to the hydroxyl group. When an asymmetric center is present, then, either $R^2$ and $R^3$ are different, or $R^4$ and $R^5$ are different, or both. The asymmetric center ultimately provides for a chiral metallocene, which can in turn be used as a catalyst to prepare chiral materials via stereospecific reactions, including stereospecific polymerization reactions.

When the amino alcohol reactant has the structural formula (IIa), it will be appreciated that the metallocene ultimately produced has the structural formula (VIII)

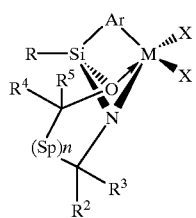
(VIII)

and is produced upon metallation of the amino alcohol-derived ligand (IX) with $MX_2Y_2$.

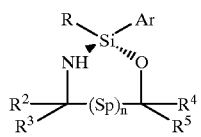
(IX)

One example of a specific embodiment of the aforementioned reaction, wherein a metallocene compound is prepared by (a) reaction of a silane reactant with an amino alcohol to provide an amino alcohol-derived ligand, and (b) metallation of the ligand, is wherein a silane reactant (V)

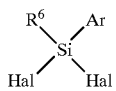
(V)

wherein Ar is cyclopentadienyl, cyclopentadienyl substituted with one to four lower alkyl groups, indenyl, fluorenyl or indolyl, $R^6$ is lower alkyl, and Hal is halide, is caused to react with an amino alcohol having the structural formula (IIa)

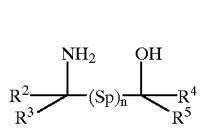
(IIa)

under conditions to promote coupling therebetween and provide the ligand (VI)

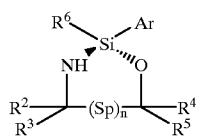
(VI)

wherein $R^2$, $R^3$, $R^4$ and $R^5$ are independently selected from the group consisting of hydrogen, lower alkyl, phenyl and benzyl, and $R^6$ is lower alkyl. The ligand (VI) is then metallated with a metal compound $MX_2Y_2$ wherein M is a Group IVA, Group VA or Group VIA metal, the X are independently selected from the group consisting of halide, lower alkoxy, lower alkyl and amido, and the Y are independently selected from the group consisting of halide and lower alkoxy, to produce the metallocene having the structural formula (VII)

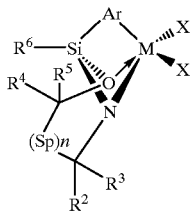
(VII)

Exemplary silane reactants include, but are not limited to, the following:

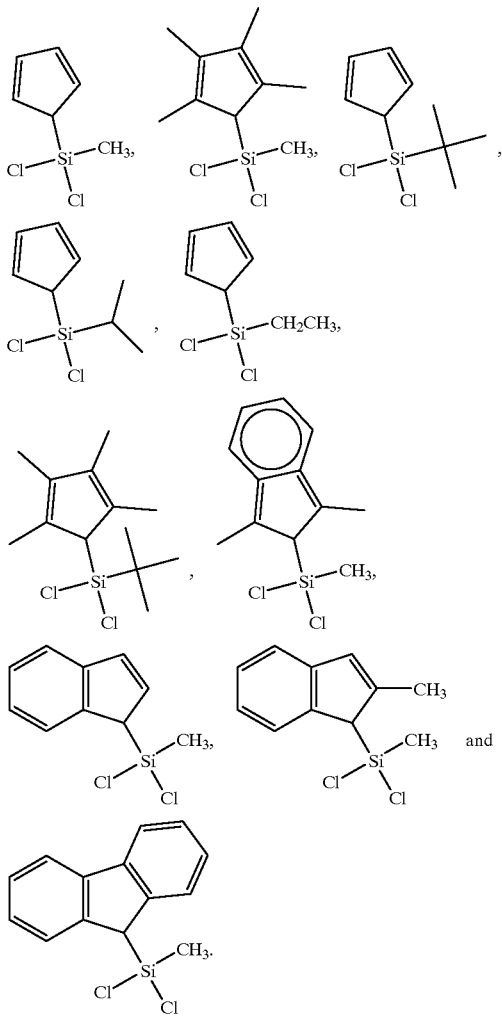

Exemplary amino alcohols include, but are not limited to, the following:

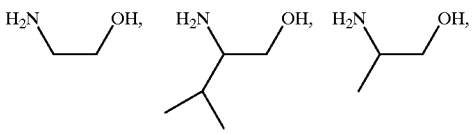

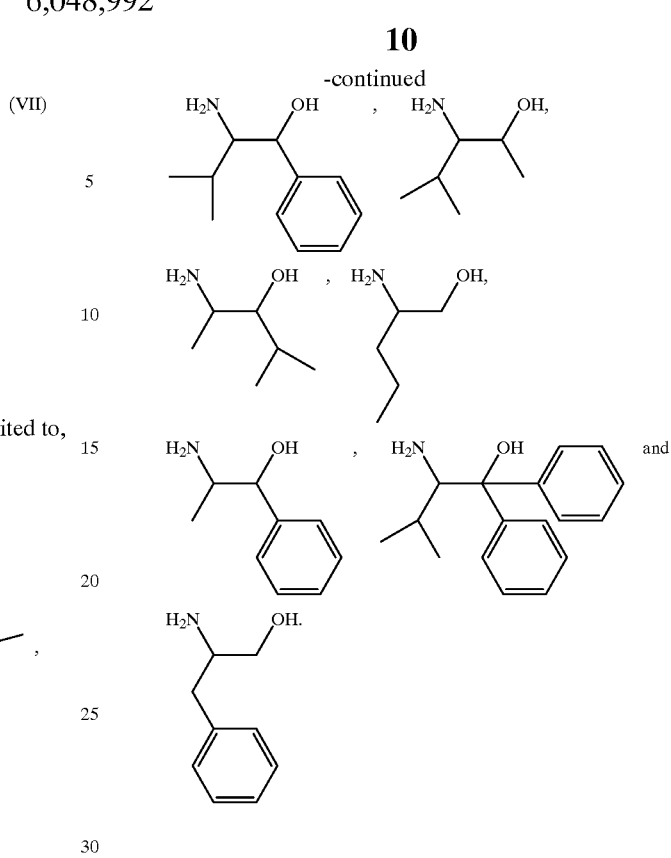

In another embodiment of the invention, an alternative method is provided for synthesizing a metallocene compound of the invention. The method initially involves reacting, in the presence of base, a silane reactant having the structural formula (Va)

(Va)

wherein Ar is cyclopentadienyl, cyclopentadienyl substituted with one to four lower alkyl groups, indenyl, fluorenyl or indolyl, $R^6$ is lower alkyl, and Hal is halide, with an amino alcohol having the structural formula (IIa)

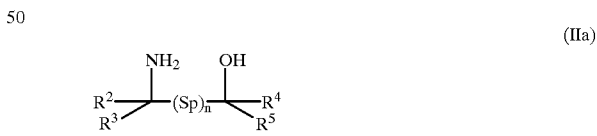
(IIa)

under conditions to promote coupling therebetween and provide intermediates (VIa) and/or (VIb)

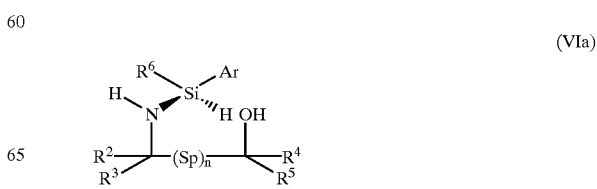
(VIa)

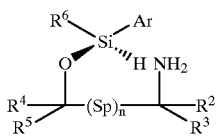

(VIb)

wherein $R^2$, $R^3$, $R^4$ and $R^5$ are independently selected from the group consisting of hydrogen, lower alkyl, phenyl and benzyl, Sp is selected from the group consisting of $—CR^7_2—$, $—CR^7_2—CR^7_2—$, $—O—$, $—S—$, $—NR^7—$, $—BR^7—$, $—C(O)—$ and combinations thereof, wherein $R^7$ is hydrogen, lower alkyl or aryl, with the proviso that Sp does not introduce more than 2 atoms between its adjacent carbon atoms, and n is 0 or 1.

The next step in the synthesis, in this embodiment, involves cyclizing the intermediates (VIa) and/or (VIb) via a catalytic dehydrocoupling reaction, to provide the ligand (VI). Dehydrocoupling may be carried out using techniques known to those skilled in the art and/or described in the pertinent literature. Generally, the intermediates are dissolved in a suitable solvent and contacted with a catalyst effective to facilitate dehydrocoupling; preferred catalysts are transition metal complexes such as $H_4Ru_4(CO)_{12}$, $Ru_3(CO)_{12}$, $Fe_3(CO)_{12}$, $Rh_6(CO)_{16}$, $Co_2(CO)_8$, $(Ph_3P)_2Rh(CO)H$, $H_2PtCl_6$, nickel cyclooctadiene, $Os_3(CO)_{12}$, $Ir_4(CO)_{12}$, $(Ph_3P)_2Ir(CO)H$, $Pd(Oac)_2$, $Cp_2TiCl_2$, $(Ph_3P)_2RhCl$, $H_2OS_3(CO)_{10}$, $Pd(Ph_3P)_4$, $Fe_3(CO)_{12}/Ru_3(CO)_{12}$, Pt/C, $Pt/BaSO_4$, Cr, Pd/C, Co/C, Pt black, Co black, Pd black, $Ir/Al_2O_3$, $Pt/SiO_2$, $Rh/TiO_2$, $Rh/La_2O_3$, Pd/Ag alloy, $LaNi_5$ and $PtO_2$. Typically, the dehydrocoupling catalyst needs to be activated by heating and/or by treatment of the reaction medium with radiation; activation may also be accomplished by the use of promoters such as acids, bases, oxidants, hydrogen or the like. The concentration of catalyst will usually be less than or equal to about 5 mole % based on the total number of moles of reactant.

Following cyclization, the ligand (VI) is metallated as described above to provide a metallocene having the structural formula (VII)

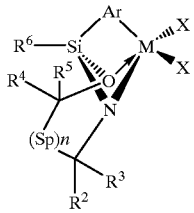

(VII)

Exemplary silane reactants for use in this latter synthesis include, but are not limited to,

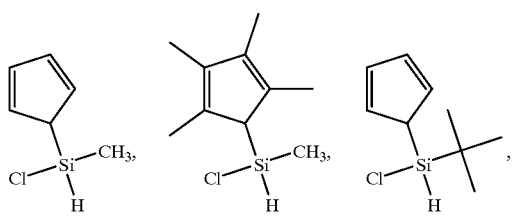

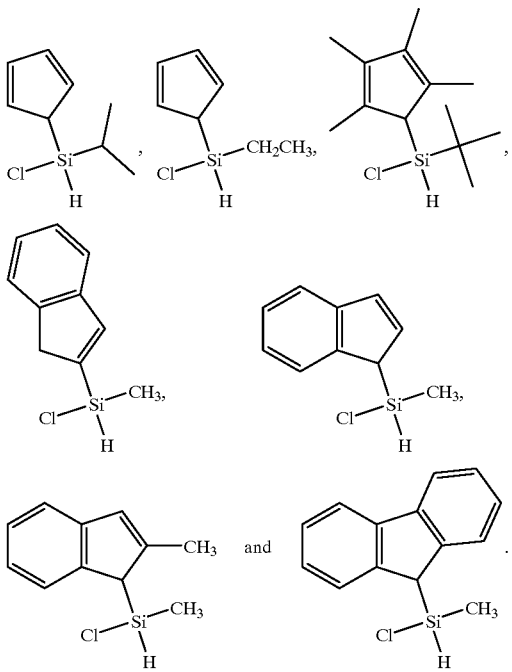

In still another embodiment of the invention, a method is provided for synthesizing an amino alcohol-derived ligand useful for preparing metallocene compounds via a metallation reaction. The method comprises reacting, in the presence of base, (i) a silane substituted with an aromatic moiety and two leaving groups with (ii) an amino alcohol, under conditions effective to promote coupling therebetween and provide a silicon-containing, nitrogen-containing ligand. Suitable silane reactants and amino alcohols are as described above.

In additional embodiments, the invention encompasses amino alcohol-derived ligands and metallocene compounds that may be prepared therefrom. That is, the invention includes as novel compositions of matter the metallocene compounds having the structural formula (VIII)

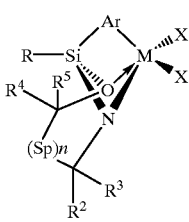

(VIII)

wherein:
Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are preferably fused;
M is a Group IVA, Group Va or Group VIA metal;
the X are independently selected from the group consisting of halide, lower alkoxy, lower alkyl and amido;
R is hydrocarbyl; and
$R^2$, $R^3$, $R^4$ and $R^5$ are independently selected from the group consisting of hydrogen, alkyl and aryl;

Sp is selected from the group consisting of —CR$^7_2$—, —CR$^7_2$—CR$^7_2$—, —O—, —S—, —NR$^7$—, —BR$^7$—, —C(O)— and combinations thereof, wherein R$^7$ is hydrogen, lower alkyl or aryl, with the proviso that Sp does not introduce more than 2 atoms between its adjacent carbon atoms, and n is 0 or 1.

In preferred metallocenes:

Ar is cyclopentadienyl, cyclopentadienyl substituted with one, two, three or four lower alkyl substituents, indenyl, fluorenyl and indolyl;

M is a Group IVA metal;

R is alkyl or alkenyl; and

R$^2$, R$^3$, R$^4$ and R$^5$ are independently selected from the group consisting of hydrogen, lower alkyl, phenyl and benzyl; and n is 0.

In particularly preferred metallocenes:

Ar is cyclopentadienyl, tetramethylcyclopentadienyl, indenyl or fluorenyl;

M is selected from the group consisting of Ti, Zr and Hf; and

R is lower alkyl or lower alkenyl.

The amino alcohol-derived ligands that represent novel compositions of matter herein have the structural formula (III)

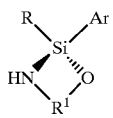

wherein R is hydrocarbyl, R$^1$ is hydrocarbylene, and Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are preferably fused. Preferred amino alcohol-derived ligands have the structural formula (IX)

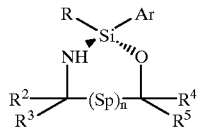

wherein:

Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are fused;

R is hydrocarbyl;

R$^2$, R$^3$, R$^4$ and R$^5$ are independently selected from the group consisting of hydrogen, alkyl and aryl;

Sp is selected from the group consisting of —CR$^7_2$—, —CR$^7_2$—CR$^7_2$—, —O—, —S—, —NR$^7$—, —BR$^7$—, —C(O)— and combinations thereof, wherein R$^7$ is hydrogen, lower alkyl or aryl, with the proviso that Sp does not introduce more than 2 atoms between its adjacent carbon atoms, and n is 0 or 1.

In particularly preferred ligands of structural formula (IX):

Ar is cyclopentadienyl, cyclopentadienyl substituted with one, two, three or four lower alkyl substituents, indenyl, fluorenyl and indolyl;

R is alkyl or alkenyl;

R$^2$, R$^3$, R$^4$ and R$^5$ are independently selected from the group consisting of hydrogen, lower alkyl, phenyl and benzyl; and n is 0.

In the most preferred ligands of structural formula (IX):

Ar is cyclopentadienyl, tetramethylcyclopentadienyl, indenyl or fluorenyl; and

R is lower alkyl or lower alkenyl.

In catalyzing polymerization, the metallocenes of the invention are normally used in conjunction with a conventional catalyst activator, as will be appreciated by those skilled in the art. Suitable catalyst activators include metal alkyls, hydrides, alkylhydrides, and alkylhalides, such as alkyllithium compounds, dialkylzinc compounds, trialkyl boron compounds, trialkylaluminum compounds, alkylaluminum halides and hydrides, and tetraalkylgermanium compounds. Specific examples of useful activators include n-butyllithium, diethylzinc, di-n-propylzinc, triethylboron, triethylaluminum, triisobutylaluminum, tri-n-hexylaluminum, ethylaluminum dichloride, dibromide and dihydride, isobutyl aluminum dichloride, dibromide and dihydride, di-n-propylaluminum chloride, bromide and hydride, diisobutylaluminum chloride, bromide and hydride, ethylaluminum sesquichloride, methyl aluminoxane ("MAO"), hexaisobutyl aluminoxane, tetraisobutyl aluminoxane, polymethyl aluminoxane, tri-n-octylaluminum, tetramethylgermanium, and the like. Other activators which are typically referred to as ionic cocatalysts may also be used; such compounds include, for example, $(C_6H_6)_3^+$, $C_6H_5$—$NH_2CH_3^+$, and tetra(pentafluorophenyl) boron. Mixtures of activators may, if desired, be used.

For liquid phase or slurry polymerization, the catalyst and activator are generally mixed in the presence of inert diluents such as, for example, aliphatic or aromatic hydrocarbons, e.g., liquified ethane, propane, butane, isobutane, n-butane, n-hexane, isooctane, cyclohexane, methylcyclohexane, cyclopentane, methylcyclopentane, cycloheptane, methylcycloheptane, benzene, ethylbenzene, toluene, xylene, kerosene, Isopar® M, Isopar® E, and mixtures thereof. Liquid olefins or the like which serve as the monomers or comonomers in the polymerization process may also serve as the diluent; such olefins include, for example, ethylene, propylene, butene, 1-hexene and the like. The amount of catalyst in the diluent will generally be in the range of about 0.01 to 1.0 mmoles/liter, with activator added such that the ratio of catalyst to activator is in the range of from about 10:1 to 1:2000, preferably in the range of from about 1:1 to about 1:200, on a molar basis.

Various additives may be incorporated into the mixture; particularly preferred additives are neutral Lewis bases such as amines, anilines and the like, which can accelerate the rate of polymerization.

Preparation of the catalyst/activator/diluent mixture is normally carried out under anhydrous conditions in the absence of oxygen, at temperatures in the range of from about −90° C. to about 300° C., preferably in the range of from about −10° C. to about 200° C.

The catalyst, activator and diluent are added to a suitable reaction vessel, in any order, although, as noted above, the catalyst and activator are usually mixed in the diluent and the mixture thus prepared then added to the reactor.

The novel catalysts may be used to prepare polymeric compositions using conventional polymerization techniques known to those skilled in the art and/or described in the pertinent literature. The monomer(s), catalyst and catalyst activator are contacted at a suitable temperature at reduced, elevated or atmospheric pressure, under an inert atmosphere, for a time effective to produce the desired polymer composition. The catalyst may be used as is or supported on a suitable support. In one embodiment, the novel metallocene compounds are used as homogeneous catalysts, i.e., as unsupported catalysts, in a gas phase or liquid phase polymerization process. A solvent may, if desired, be employed. The reaction may be conducted under solution or slurry conditions, in a suspension using a perfluorinated hydrocarbon or similar liquid, in the gas phase, or in a solid phase powder polymerization.

Liquid phase polymerization generally involves contacting the monomer or monomers with the catalyst/activator mixture in the polymerization diluent, and allowing reaction to occur under polymerization conditions, i.e., for a time and at a temperature sufficient to produce the desired polymer product. Polymerization may be conducted under an inert atmosphere such as nitrogen, argon, or the like, or may be conducted under vacuum. Preferably, polymerization is conducted in an atmosphere wherein the partial pressure of reacting monomer is maximized. Liquid phase polymerization may be carried out at reduced, elevated or atmospheric pressures. In the absence of added solvent, i.e., when the olefinic monomer serves as the diluent, elevated pressures are preferred. Typically, high pressure polymerization in the absence of solvent is carried out at temperatures in the range of about 180° C. to about 300° C., preferably in the range of about 250° C. to about 270° C., and at pressures on the order of 200 to 20,000 atm, typically in the range of about 1000 to 3000 atm. When solvent is added, polymerization is generally conducted at temperatures in the range of about 150° C. to about 300° C., preferably in the range of about 220° C. to about 250° C., and at pressures on the order of 10 to 2000 atm.

Polymerization may also take place in the gas phase, e.g., in a fluidized or stirred bed reactor, using temperatures in the range of approximately 60° C. to 120° C. and pressures in the range of approximately 10 to 1000 atm.

The monomer or comonomers used are addition polymerizable monomers containing one or more degrees of unsaturation. Olefinic or vinyl monomers are preferred, and particularly preferred monomers are α-olefins having from about 2 to about 20 carbon atoms, such as, for example, linear or branched olefins including ethylene, propylene, 1-butene, 3-methyl-1-butene, 1,3-butadiene, 1-pentene, 4-methyl-1-pentene, 1-hexene, 4-methyl-1-hexene, 1,4-hexadiene, 1,5-hexadiene, 1-octene, 1,6-octadiene, 1-nonene, 1-decene, 1,4-dodecadiene, 1-hexadecene, 1-octadecene, and mixtures thereof. Cyclic olefins and diolefins may also be used; such compounds include, for example, cyclopentene, 3-vinylcyclohexene, norbornene, 5-vinyl-2-norbornene, 5-ethylidene-2-norbornene, dicyclopentadiene, 4-vinylbenzocyclobutane, tetracyclododecene, dimethano-octahydronaphthalene, and 7-octenyl-9-borabicyclo-(3,3,1)nonane. Aromatic monomers which may be polymerized using the novel metallocenes include styrene, o-methylstyrene, m-methylstyrene, p-methylstyrene, p-tert-butylstyrene, m-chlorostyrene, p-chlorostyrene, p-fluorostyrene, indene, 4-vinylbiphenyl, acenaphthalene, vinylfluorene, vinylanthracene, vinylphenanthrene, vinylpyrene and vinylchrisene. Other monomers which may be polymerized using the present catalysts include methylmethacrylate, ethylacrylate, vinyl silane, phenyl silane, trimethylallyl silane, acrylonitrile, maleimide, vinyl chloride, vinylidene chloride, tetrafluoroethylene, isobutylene, carbon monoxide, acrylic acid, 2-ethylhexylacrylate, methacrylonitrile and methacrylic acid.

In gas and slurry phase polymerizations, the catalyst is used in a heterogeneous process, i.e., supported on an inert inorganic substrate. Conventional materials can be used for the support, and are typically particulate, porous materials; examples include oxides of silicon and aluminum, or halides of magnesium and aluminum. Particularly preferred supports from a commercial standpoint are silicon dioxide and magnesium dichloride.

The polymeric product resulting from the aforementioned reaction may be recovered by filtration or other suitable techniques. If desired, additives and adjuvants may be incorporated into the polymer composition prior to, during, or following polymerization; such compounds include, for example, pigments, antioxidants, lubricants and plasticizers.

The novel metallocenes of the invention are also useful in catalyzing other types of reactions, i.e., reactions other than polymerizations. Such reactions include, but are not limited to, hydrogenation, dehydrocoupling, cyclization, substitution, carbomagnesation and hydrosilylation. Methods for using metallocenes to catalyze the aforementioned reactions and others will be known to those skilled in the art and/or described in the pertinent texts and literature.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains.

The following examples are put forth so as to provide those of ordinary skill in the art with a complete disclosure and description of how to make and use the compounds of the invention, and are not intended to limit the scope of that which the inventors regard as their invention.

All patents, patent applications and publications cited herein are incorporated by reference in their entireties.

EXAMPLE 1

SYNTHESIS OF REPRESENTATIVE AMINO ALCOHOLS

A. Synthesis of (S)-(−)-2-Amino-3-methyl-1,1-diphenylbutan-1-ol

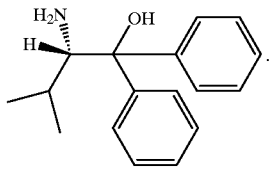

The above amino alcohol is synthesized according to the method of Itauno et al. (1984)*J. Org. Chem.* 49:555–557. The Grignard reagent phenylmagnesium bromide is prepared from bromobenzene (0.5 mol) and magnesium (0.7 mol) in dry THF using standard procedures. (S)-Valine methyl ester hydrochloride (0.1 mol) is added dropwise to the THF solution of phenylmagnesium bromide at 0° C., and the resulting mixture is stirred at room temperature for 5 h. An ammonium hydrochloride solution is then added, the THF layer separated, and the aqueous layer extracted four times with ethyl acetate. The combined organic layers are dried over anhydrous. MgSO$_4$, the solvent removed under reduced pressure, and the solid recrystallized from ethanol-water (10:1 v/v) to give the amino alcohol as a colorless solid.

B. Synthesis of (S)-(−)-2-Amino-3,1-dimethylbutan-1-ol

The amino alcohol is made by the procedure described above in part (A), except that (S)-valine methyl ester hydrochloride is reacted with a molar equivalent of methyl magnesium bromide instead of phenylmagnesium bromide.

C. Synthesis of 2-amino-3-methyl-1-butanol

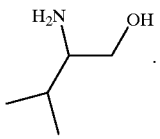

Valine methyl ester (0.1 mol) is dissolved in dry THF, and NaBH$_4$ (0.035 mol) is then added slowly. The reaction mixture is stirred at room temperature for about 4 hours, and the colorless solid is purified by the procedure described in part (A).

EXAMPLE 2

METALLOCENE PREPARATION

A. A Metallocene Compound Having the Structure

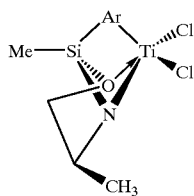

wherein "Ar" is tetramethylcyclopentadienyl, was prepared as follows.

(2,3,4,5-Tetramethylcyclopentadienyl)lithium (1.33 g, 10.37 mmol) was dissolved in 80 mL THF and cooled to −78° C., and MeSiCl$_3$ (1.70 g, 11.4 mmol) was added via a syringe. After addition, the cooling bath was removed and the reaction mixture was stirred at room temperature for 16 h. Volatiles were removed under vacuum at room temperature, and the residue was extracted twice with hexanes (2×20 mL). The hexane fractions were combined and the solvent was removed under vacuum to give a pale yellow oil (tetramethylcyclopentadienyl methyl silicon dichloride); 2.0 g, 82% yield. $^1$H-NMR (C$_6$D$_6$): δ(ppm): 2.95 (broad s, 1 H; Me$_4$CpH), 1.92 (s, 6H;), 1.63 (s, 6H; Me$_4$Cp), 0.19 (s, 3 H; MeSi).

A three-neck 250 mL round bottom flask equipped with 2 addition funnels was charged with diethyl ether (25 mL) and triethylamine (1.2 mL, 8.5 mmol). In one of the addition funnels was placed tetramethylcyclopentadienyl methyl silicon dichloride (1.0 g, 4.25 mmol), prepared above, dissolved in 20 mL diethyl ether, and in the other addition funnel was placed 2-amino-1-propanol (0.320 g, 4.25 mmol) dissolved in 20 mL diethyl ether. The solutions of the two addition funnels were added simultaneously to the reaction flask containing triethylamine. A white precipitate formed immediately. The reaction mixture was stirred for 4 hours followed by removal of the solvent under vacuum. The resulting yellow oily precipitate is extracted with 100 mL hexanes, and the resulting yellow solution was concentrated to around 5 mL volume. $^1$H-NMR (C$_6$D$_6$): δ(ppm): 3.9–2.9 (broad m, 4 H); —CH$_2$—O, CMeH—N, Me$_4$CpH), 2.4–1.8 (broad m, 12 H; Me$_4$Cp), 0.37 (s, 3 H; MeSi).

To 0.1 mol of the product thus prepared dissolved in 50 mL THF at 0° C. was slowly added n-butyllithium (20 mL of 10 M in hexane), and the solution was left to stir at 0° C. for 1 h. To the solution was gradually added zirconium tetrachloride (0.1 mol) slurried in 65 mL diethyl ether. The mixture was allowed to stir for 18 h at room temperature. The solvent was then removed. The solid was extracted with 20 mL toluene and filtered. The toluene was removed to yield a pale yellow powder. The product was characterized with NMR, by its IR spectra, and by elemental analysis.

B. Alternative Synthesis

In an alternative synthesis of the above metallocene, Me(RCp)SiCl$_2$ (4 mmol; R=2,3,4,5-Me$_4$) is dissolved in diethyl ether or tetrahydropyran, and dimethylamine (16 mmol) is slowly added. The reaction is stirred overnight, and the dimethylamine hydrochloride precipitate is separated from Me(RCp)Si(NMe2)$_2$. Then, equimolar Me(RCp)Si(NMe$_2$)$_2$ and an α-aminoalcohol, 2-amino-1-propanol are reacted by dissolving in a solvent, or as a neat solution. The reaction produces dimethylamine that is flushed out using a moderate flow of nitrogen. The resultant product is treated as above in section A.

It will be appreciated that this method may be conducted using other amino alcohols such as those having the formula HO—CH$_2$—CHR'—NH$_2$, wherein R'=Et, iPr, $^t$Bu, phenyl, or the like, and/or other substituted silanes such as those having the formula Me(RCp)SiCl$_2$ where R may be, for example, 2,3-(CH$_2$)$_4$, 2-Me, 3-Me, and the like. Other solvents may of course be used as well.

C. A Metallocene having the Structural Formula

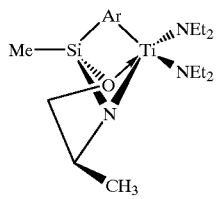

wherein Ar is tetramethylcyclopentadienyl, is prepared as follows.

The silane (0.1 mol) synthesized in step A above is dissolved in THF followed by the addition of Ti(NEt$_2$)$_4$ (0.1 mol). The reaction mixture is stirred overnight at room temperature. The solvent is then removed under reduced pressure, and the solid is extracted with 20 mL toluene and filtered. The toluene is removed to yield a pale yellow powder. The product is characterized with NMR, by its IR spectra, and by elemental analysis.

D. A Metallocene having the Structural Formula

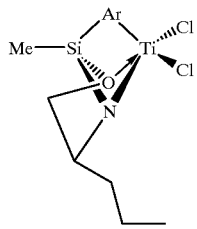

wherein Ar is tetramethylcyclopentadienyl, is prepared as follows.

Tetramethylcyclopentadiene (0.1 mol) is dissolved in 100 mL THF and cooled to −78° C. n-Butyllithium (50 mL of 2.2M in hexane) is added dropwise. The mixture is allowed to warm to room temperature and stirred for 1 h. The resulting suspension is then cooled to −30° C. and 10.4 mL of MeSiHCl$_2$ is added over 10 minutes. The mixture is allowed to warm to room temperature to give a colorless solution. The solution is then stirred at room temperature overnight. The solution is then filtered and concentrated to dryness. The solid is then extracted with pentane and filtered. The pentane was removed to give the colorless chlorosilane as a solid.

2-Amino- 1 -pentanol (0.1 mol) is dissolved in 45 mL THF, n-butyllithium (20 mL of 10 M in hexane) is then added slowly, and the solution left to stir at 0° C. for 4 h. To this solution chlorosilane (0.1 mol, prepared above) dissolved in 25 mL of THF is slowly added. The solution is then warmed to room temperature, stirred overnight and the solvents then removed. The solid is extracted with pentane, filtered, and the pentane removed. The silane is dissolved in 50 mL of hexane, 0.05 g of 5% palladium on carbon is then added, and the solution refluxed for 1 hour. The solution is cooled to room temperature, filtered, and the solvent removed to give a colorless solid.

To the solid prepared above (0.1 mol) dissolved in 50 mL THF at 0° C., n-butyllithium (20 mL of 10 M in hexane) is then added slowly, and the solution left to stir at 0° C. for 1 h. To the solution is gradually added zirconium tetrachloride (0.1 mol) slurried in 65 mL diethyl ether. The mixture is allowed to stir for 18 h at room temperature. The solvent is then removed. The solid is extracted with 20 mL toluene and filtered. The toluene is removed to yield a pale yellow solid. The product is characterized with NMR, by its IR spectra, and by elemental analysis.

EXAMPLE 3

CATALYSIS OF POLYMERIZATION

A. Polymerization of Polyethylene

The metallocene compounds prepared in Example 2 are used as polymerization catalysts in the preparation of polyethylene ("PE"). Polymerizations are conducted in a 300 mL autoclave reactor. Methyl aluminoxane ("MAO") is used as co-catalyst with total Al/M ratio equal to 1000. The reactor is loaded with 150 mL of toluene and the MAO, and then heated to 80° C. and pressurized with ethylene to 40 psig. The reactor is configured to maintain the set pressure and temperature during the polymerization reaction. The reaction is initiated by injection of the catalyst. The reactions are run for 30 minutes and terminated by injection of acidified methanol (2% HCl). The polymer is removed from the reactor and washed with additional acidified methanol, aqueous NaHCO$_3$, water, and acetone, and dried in a vacuum oven overnight.

B. Dehydrocoupling Reaction of Polyhydridomethylsilazane with Hexene

Polyhydridomethylsilazane (PHMSO) is a linear polymer ([MeHSiO]$_x$) with a molecular weight of about 2000, thus containing about 33 Si—H units, and having a viscosity of about 30 cS. Two grams of [MeHSiO]$_x$, equaling about 33 mmol Si—H, is mixed with 4.15 ml 1-hexene (33 mmol) and the catalyst prepared in part (B) of Example 2 (1 mg). The reaction is allowed to proceed overnight at room temperature. The extent of Si—H bonds consumed is determined by NMR.

C. Dehydrocoupling Reaction of Polyhydridomethylsilazane with 2-dimethylaminoethanol The procedure of part (B) is repeated using 5 g PHMSO, 8 mL 2-dimethylaminoethanol (80 mmol), and the catalyst prepared in part (B) of Example 2 (2 mg) at room temperature, so as to yield the dehydrocoupling product in which Si—H groups are replaced with Si—O—CH$_2$CH$_2$NMe$_2$ groups. The polymeric product is found to be soluble in acidic solution but precipitates within 1- with with Si—O—CH$_2$CH$_2$NMe$_2$ groups. The polymeric product is found to be soluble in acidic solution but precipitates within 1–2 hours. The polymeric product can be reacted with dry HCl gas in a solvent such as toluene or diethylether or the like to precipitate a white solid. This solid thus obtained is soluble in water and characterized by NMR.

EXAMPLE 4

STEREOSPECIFIC CATALYSIS

The polymers obtained with the stereospecific catalysts prepared in Example 2 exhibit increased crystallinity and a higher deformation temperature compared with polymers obtained using conventional Ziegler-Natta catalysts.

A 300 mL autoclave reactor was loaded with 150 ML of liquid propylene and heated to 50° C. In a drybox, 1×10$^{-3}$ mmol of the metallocene compound prepared in part (A) was mixed with 1 mmol of MAO in toluene. The solution was allowed to stir for 15 minutes. The catalyst solution was then transferred to a catalyst injection tube. The injection tube was connected to the reactor and the catalyst solution was injected using an overpressure of argon. The total catalyst activation time was 30 minutes. The reactor temperature was maintained at 50° C. to 52° C. The polymerization reaction was quenched after one hour with methane (10 mL) and the remaining propylene quickly vented. Toluene (150 mL) was added and the reactor heated to 110° C. for 30 minutes. The reactor was cooled to 70° C., opened, and the polymer solution poured into a one-gallon bucket containing 1-L of methanol. The polymer was collected by filtration and dried at 40° C. under vacuum for 16 h.

We claim:

1. A method for synthesizing a metallocene compound, comprising the steps of:
   (a) reacting, in the presence of base, (i) a silane substituted with an aromatic moiety and two leaving groups with (ii) an amino alcohol, under conditions effective to promote coupling therebetween and provide a silicon-containing, nitrogen-containing ligand; and
   (b) contacting the ligand with a metal compound under reaction conditions effective to bring about metallation.

2. The method of claim 1, wherein the amino alcohol contains at least one asymmetric center.

3. The method of claim 1, wherein following step (a) and prior to step (b), the ligand is treated with a reagent effective to remove two hydrogen atoms.

4. A method for synthesizing a metallocene compound, comprising the steps of:
   (a) reacting, in the presence of base, a silane reactant having the structural formula (I)

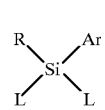

(I)

with an amino alcohol having the structural formula (II)

under conditions to promote coupling therebetween and provide the ligand (III)

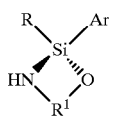
(III)

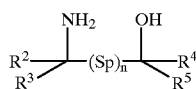
(IIa)

wherein the L are independently leaving groups, R is hydrocarbyl, $R^1$ is hydrocarbylene, and Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are fused; and (b) contacting the ligand with a metal compound $MX_2Y_2$ wherein M is a Group IVA, Group VA or Group VIA metal, the X are independently selected from the group consisting of halide, lower alkoxy, lower alkyl and amido, and the Y are independently selected from the group consisting of halide and lower alkoxy, to provide a metallocene compound having the structural formula (IV)

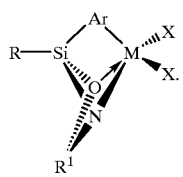
(IV)

5. The method of claim 4, wherein following step (a) and prior to step (b), the ligand is treated with a reagent effective to remove two hydrogen atoms.

6. The method of claim 5, wherein the reagent is an organolithum compound, an organotin compound, or a Grignard reagent.

7. The method of claim 5, wherein, in the silane reactant (I):
Ar is cyclopentadienyl, cyclopentadienyl substituted with one, two, three or four lower alkyl substituents, indenyl, fluorenyl or indolyl;
L is hydrido, alkoxy or halide; and
R is alkyl or alkenyl.

8. The method of claim 7, wherein, in the silane reactant (I):
Ar is cyclopentadienyl, tetramethylcyclopentadienyl, indenyl or fluorenyl;
L is lower alkoxy or chloro;
R is lower alkyl or lower alkenyl.

9. The method of claim 1, wherein M is a Group IVA metal.

10. The method of claim 9, wherein, M is selected from the group consisting of Ti, Zr and Hf.

11. The method of claim 8, wherein M is a Group IVA metal.

12. The method of claim 11, wherein M is selected from the group consisting of Ti, Zr and Hf.

13. The method of claim 5, wherein the amino alcohol (II) contains at least one asymmetric center.

14. The method of claim 13, wherein the asymmetric center is at a carbon atom.

15. The method of claim 4, wherein the amino alcohol (II) has the structural formula (IIa)

wherein $R^2$, $R^3$, $R^4$ and $R^5$ are independently selected from the group consisting of hydrogen, alkyl and aryl, Sp is an optionally substituted spacer group, and n is 0 or 1.

16. The method of claim 15, wherein $R^2$, $R^3$, $R^4$ and $R^5$ are independently selected from the group consisting of hydrogen, lower alkyl, phenyl and benzyl, and n is O.

17. The method of claim 16, wherein one of $R^2$ and $R^3$ is hydrogen and the other is lower alkyl.

18. The method of claim 12, wherein the amino alcohol (II) has the structural formula (IIa)

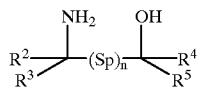
(IIa)

wherein $R^2$, $R^3$, $R^4$ and $R^5$ are independently selected from the group consisting of hydrogen, alkyl and aryl, Sp is an optionally substituted spacer group, and n is 0 or 1.

19. The method of claim 18, wherein $R^2$, $R^3$, $R^4$ and $R^5$ are independently selected from the group consisting of hydrogen, lower alkyl, phenyl and benzyl, and n is 0.

20. The method of claim 19, wherein one of $R^2$ and $R^3$ is hydrogen and the other is lower alkyl.

21. A method for synthesizing a metallocene compound, comprising the steps of:

a) reacting, in the presence of base, a silane reactant having the structural formula (V)

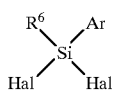
(V)

wherein Ar is cyclopentadienyl, cyclopentadienyl substituted with one to four lower alkyl groups, indenyl, fluorenyl or indolyl, $R^6$ is lower alkyl, and Hal is halide, with an amino alcohol having the structural formula (IIa)

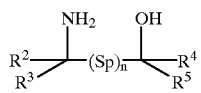
(IIa)

wherein Sp is an optionally substituted spacer group and n is 0 or 1, under conditions to promote coupling therebetween and provide the ligand (VI)

(VI)

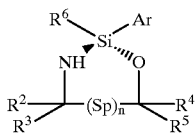

wherein $R^2$, $R^3$, $R^4$ and $R^5$ are independently selected from the group consisting of hydrogen, lower alkyl, phenyl and benzyl;

Sp is selected from the group consisting of —$CR^7_2$—, —$CR^7_2$—$CR^7_2$—, —O—, —S—, —$NR^7$—, —$BR^7$—, —C(O)— and combinations thereof, wherein $R^7$ is hydrogen, lower alkyl or aryl, with the proviso that Sp does not introduce more than 2 atoms between its adjacent carbon atoms, and n is 0 or 1;

(b) contacting the ligand with a reagent selected from the group consisting of organolithium compounds, organotin compounds, and Grignard reagents; and then (c) contacting the ligand with a metal compound $MX_2Y_2$ wherein M is a Group IVA, Group VA or Group VIA metal, the X are independently selected from the group consisting of halide, lower alkoxy, lower alkyl and amido, and the Y are independently selected from the group consisting of halide and lower alkoxy, to produce the metallocene compound having the structural formula (VII)

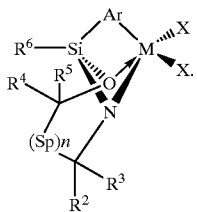

(VII)

22. The method of claim 21, wherein M is a Group IVA metal.

23. The method of claim 22, wherein M is selected from the group consisting of Ti, Zr and Hf.

24. A method for synthesizing a metallocene compound, comprising the steps of:

(a) reacting, in the presence of base, a silane reactant having the structural formula (Va)

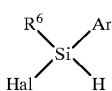

(Va)

wherein Ar is cyclopentadienyl, cyclopentadienyl substituted with one to four lower alkyl groups, indenyl, fluorenyl or indolyl, $R^6$ is lower alkyl, and Hal is halide, with an amino alcohol having the structural formula (IIa)

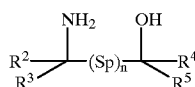

(IIa)

under conditions to promote coupling therebetween and provide the intermediates (VIa) and/or (VIb)

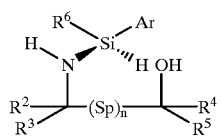

(VIa)

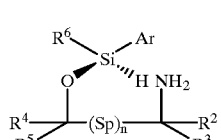

(VIb)

wherein:

$R^2$, $R^3$, $R^4$ $R^2$, $R^3$, $R^4$ and $R^5$ are independently selected from the group consisting of hydrogen, lower alkyl, phenyl and benzyl;

Sp is selected from the group consisting of —$CR^7_2$—, —$CR^7_2$—$CR^7_2$—, —O—, —S—, —$NR^7$—, —$BR^7$—, —C(O)— and combinations thereof, wherein $R^7$ is hydrogen, lower alkyl or aryl, with the proviso that Sp does not introduce more than 2 atoms between its adjacent carbon atoms, and n is 0 or 1; and (b) cyclizing the intermediates via a catalytic dehydrocoupling reaction, followed by metallation with a metal compound $MX_2Y_2$, wherein M is a metal, the X are independently halide, lower alkoxy, lower alkyl or amido, and the Y are independently halide or lower alkoxy, to provide the metallocene compound having the structural formula (VII)

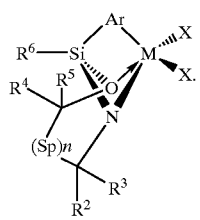

(VII)

25. A method for making an amino alcohol-derived ligand suitable for preparing a metallocene compound via metallation, comprising reacting, in the presence of base, (i) a silane substituted with an aromatic moiety and two leaving groups with (ii) an amino alcohol, under conditions effective to promote coupling therebetween and provide a silicon-containing, nitrogen-containing ligand.

26. The method of claim 25, wherein the amino alcohol contains at least one asymmetric center.

27. A method for making an amino alcohol-derived ligand suitable for preparing a metallocene compound via metallation, comprising reacting, in the presence of base, a silane reactant having the structural formula (I)

(I)

with an amino alcohol having the structural formula (II)

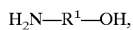
(II)

under conditions to promote coupling therebetween and provide the ligand (III)

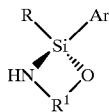
(III)

wherein the L are independently leaving groups, R is hydrocarbyl, $R^1$ is hydrocarbylene, and Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are fused.

28. The method of claim 27, wherein, in the silane reactant (I):

Ar is cyclopentadienyl, cyclopentadienyl substituted with one, two, three or four lower alkyl substituents, indenyl, fluorenyl or indolyl;

L is hydrido, alkoxy or halide; and

R is alkyl or alkenyl.

29. The method of claim 28, wherein, in the silane reactant (I):

Ar is cyclopentadienyl, tetramethylcyclopentadienyl, indenyl or fluorenyl;

L is lower alkoxy or chloro;

R is lower alkyl or lower alkenyl.

30. The method of claim 29, wherein the amino alcohol (II) has the structural formula (IIa)

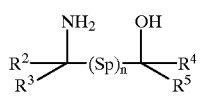
(IIa)

wherein $R^2$, $R^3$, $R^4$ and $R^5$ are independently selected from the group consisting of hydrogen, alkyl and aryl, Sp is an optionally substituted spacer group, and n is 0 or 1.

31. The method of claim 29, wherein $R^2$, $R^3$, $R^4$ and $R^5$ are independently selected from the group consisting of hydrogen, lower alkyl, phenyl and benzyl, and n is O.

32. The method of claim 31, wherein one of $R^2$ and $R^3$ is hydrogen and the other is lower alkyl.

33. A method for making an amino alcohol-derived ligand suitable for preparing a metallocene compound via metallation, comprising reacting, in the presence of base, a silane reactant having the structural formula (V)

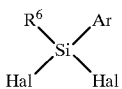
(V)

wherein Ar is cyclopentadienyl, cyclopentadienyl substituted with one to four lower alkyl groups, indenyl, fluorenyl or indolyl, $R^6$ is lower alkyl, and Hal is halide, with an amino alcohol having the structural formula (IIa)

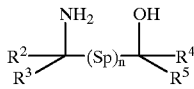
(IIa)

under conditions to promote coupling therebetween and provide the ligand (VI)

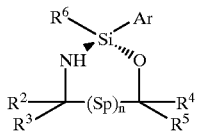
(VI)

wherein $R^2$, $R^3$, $R^4$ and $R^5$ are independently selected from the group consisting of hydrogen, lower alkyl, phenyl and benzyl, Sp is selected from the group consisting of —$CR^7_2$—, —$CR^7_2$—$CR^7_2$—, —O—, —S—, —$NR^7$—, —$BR^7$—, —C(O)— and combinations thereof, wherein $R^7$ is hydrogen, lower alkyl or aryl, with the proviso that Sp does not introduce more than 2 atoms between its adjacent carbon atoms, and n is 0 or 1.

34. A metallocene compound having the structural formula (VIII)

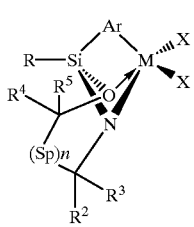
(VIII)

wherein:

Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are fused;

M is a Group IVA, Group VA or Group VIA metal;

the X are independently selected from the group consisting of halide, lower alkoxy, lower alkyl and amido;

R is hydrocarbyl; and $R^2$, $R^3$, $R^4$ and $R^5$ are independently selected from the group consisting of hydrogen, alkyl and aryl; and Sp is selected from the group consisting of —$CR^7_2$—, —$CR^7_2$—$CR^7_2$—, —O—, —S—, —$NR^7$—, —$BR^7$—, —C(O)— and combinations thereof, wherein $R^7$ is hydrogen, lower alkyl or aryl, with the proviso that Sp does not introduce more than 2 atoms between its adjacent carbon atoms, and n is 0 or 1.

35. The metallocene compound of claim 34, wherein:

Ar is cyclopentadienyl, cyclopentadienyl substituted with one, two, three or four lower alkyl substituents, indenyl, fluorenyl and indolyl;

M is a Group IVA metal;

R is alkyl or alkenyl;

$R^2$, $R^3$, $R^4$ and $R^5$ are independently selected from the group consisting of hydrogen, lower alkyl, phenyl and benzyl; and n is O.

36. The metallocene compound of claim 35, wherein:

Ar is cyclopentadienyl, tetramethylcyclopentadienyl, indenyl or fluorenyl;

M is selected from the group consisting of Ti, Zr and Hf; and

R is lower alkyl or lower alkenyl.

37. The metallocene compound of claim 34, supported on an inert inorganic support material.

38. The metallocene compound of claim 37, wherein the support material is comprised of a porous, particulate solid.

39. The metallocene compound of claim 38, wherein the support material is comprised of silicon dioxide.

40. The metallocene compound of claim 38, wherein the support material is comprised of aluminum oxide.

41. An amino alcohol-derived ligand suitable for preparing a metallocene compound via metallation, comprising a compound having the structural formula (III)

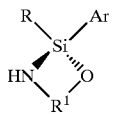

(III)

wherein R is hydrocarbyl, $R^1$ is hydrocarbylene, and Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are fused.

42. An amino alcohol-derived ligand suitable for preparing a metallocene compound via metallation, comprising a compound having the structural formula (IX)

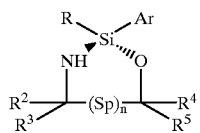

(IX)

wherein:

Ar is an aromatic moiety containing 1 to 3 aromatic rings with at least 1 of the aromatic rings comprising a cyclopentadienyl group, wherein Ar is optionally substituted with an alkyl or aryl substituent, and further wherein if Ar contains 2 or 3 aromatic rings, the rings are fused;

R is hydrocarbyl; and $R^2$, $R^4$ and $R^5$ are independently selected from the group consisting of hydrogen, alkyl and aryl; and Sp is selected from the group consisting of $-CR^7{}_2-$, $-CR^7{}_2-CR^7{}_2-$, $-O-$, $-S-$, $-NR^7-$, $-BR^7-$, $-C(O)-$ and combinations thereof, wherein $R^7$ is hydrogen, lower alkyl or aryl, with the proviso that Sp does not introduce more than 2 atoms between its adjacent carbon atoms, and n is 0 or 1.

43. The ligand of claim 42, wherein:

Ar is cyclopentadienyl, cyclopentadienyl substituted with one, two, three or four lower alkyl substituents, indenyl, fluorenyl and indolyl;

R is alkyl or alkenyl; and $R^2$, $R^3$, $R^4$ and $R^5$ are independently selected from the group consisting of hydrogen, lower alkyl, phenyl and benzyl; and n is O.

44. The ligand of claim 43, wherein:

Ar is cyclopentadienyl, tetramethylcyclopentadienyl, indenyl or fluorenyl; and

R is lower alkyl or lower alkenyl.

45. A method for preparing a polymer composition, comprising:

contacting, under polymerization conditions, one or more addition polymerizable monomers having at least one degree of unsaturation with the metallocene compound of claim 34.

46. A method for preparing a polymer composition, comprising:

contacting, under polymerization conditions, one or more addition polymerizable monomers having at least one degree of unsaturation with the metallocene compound of claim 35.

47. A method for preparing a polymer composition, comprising:

contacting, under polymerization conditions, one or more addition polymerizable monomers having at least one degree of unsaturation with the metallocene compound of claim 36.

48. A method for preparing a polymer composition, comprising:

contacting, under polymerization conditions, one or more addition polymerizable monomers having at least one degree of unsaturation with the metallocene compound of claim 37.

* * * * *